United States Patent [19]

Dore

[11] 4,017,478
[45] Apr. 12, 1977

[54] WATER-SOLUBLE AZO DYES HAVING A 2-ACETOACETAMIDOFLUORENYL COUPLING COMPONENT RADICAL

[75] Inventor: Jacky Dore, Basel, Switzerland
[73] Assignee: Sandoz Ltd., Basel, Switzerland
[22] Filed: Sept. 6, 1974
[21] Appl. No.: 503,967

Related U.S. Application Data

[62] Division of Ser. No. 40,355, May 25, 1970, abandoned.

[30] Foreign Application Priority Data

June 2, 1969 Switzerland .................. 8335/69
June 20, 1969 Switzerland .................. 9463/69

[52] U.S. Cl. .................. 260/158; 8/26;
260/146 R; 260/147; 260/156; 260/160;
260/161; 260/176; 260/178; 260/193
[51] Int. Cl.² .................. C09B 29/32; C09B 31/10;
C09B 35/20; C09B 45/28
[58] Field of Search .......... 260/152, 153, 154, 155,
260/156, 157, 158, 162, 163, 159, 160, 161;
8/26

[56] References Cited

UNITED STATES PATENTS

| | | | |
|---|---|---|---|
| 1,506,514 | 8/1924 | Zitscher | 260/158 |
| 1,976,185 | 10/1934 | Muller et al. | 260/152 |
| 2,016,726 | 11/1935 | Richardson | 260/188 UX |
| 2,026,908 | 1/1936 | Muth | 260/152 |
| 2,032,627 | 3/1936 | Muth | 260/152 |
| 2,061,126 | 11/1936 | Zahn et al. | 260/152 X |
| 2,128,508 | 8/1938 | Stusser et al. | 260/152 |
| 2,138,553 | 11/1938 | Muth | 260/152 X |
| 2,305,095 | 12/1942 | Mackenzie | 260/149 |
| 2,617,798 | 11/1952 | Mueller et al. | 260/193 |
| 2,662,913 | 12/1953 | Eberhardt et al. | 260/507 |
| 2,857,373 | 10/1958 | Straley et al. | 260/146 R |
| 2,871,234 | 1/1959 | Bergstrom | 260/162 |
| 3,036,059 | 5/1962 | Ehrhardt et al. | 260/149 |
| 3,079,376 | 2/1963 | Bergstrom | 260/192 |
| 3,478,010 | 11/1969 | Hoffmann et al. | 260/152 |
| 3,609,134 | 9/1971 | Mory | 260/152 |
| 3,825,527 | 7/1974 | Ruider et al. | 260/152 |

FOREIGN PATENTS OR APPLICATIONS 789,704 11/1935 France .................. 260/193

OTHER PUBLICATIONS

Hughes et al., Chemical Abstracts, vol. 33, 609–610 (1939).
Miller et al., Chemical Abstracts, vol. 58, 1787–1788 (1963).

*Primary Examiner*—Floyd D. Higel
*Attorney, Agent, or Firm*—Gerald D. Sharkin; Richard E. Vila; Melvyn M. Kassenoff

[57] ABSTRACT

Dyes of the formula

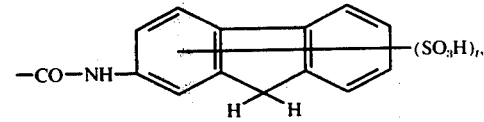

wherein
D is a carbocyclic aryl or heterocyclic aryl diazo component radical,
q is 0 to 3, and
t is 0, 1 or 2,
with the proviso that $q + t$ is 1 to 5, are highly
the dyeing, padding and printing of textile fibers and textiles of natural or regenerated cellulose and paper. The dyes build-up well, exhibit good fastness to wet treatments, alcohol, light, rubbing and dry cleaning and are resistant to acids and alkalis.

13 Claims, No Drawings

WATER-SOLUBLE AZO DYES HAVING A 2-ACETOACETAMIDOFLUORENYL COUPLING COMPONENT RADICAL

This application is a division of application Ser. No. 40,355, filed May 25, 1970 and now abandoned.

This invention is directed to new azo dyes containing sulphonic acid groups and the metal complex compounds of these dyes, which bear a radical of the formula

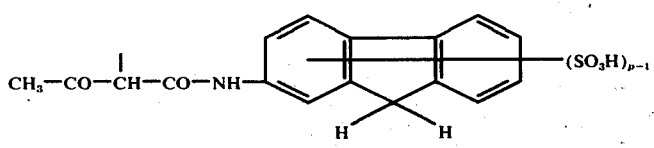

where $p$ represents 1, 2 or 3, and which are highly suitable for the dyeing, padding and printing of textile fibres and textiles of natural or regenerated cellulose.

The invention thus relates to new azo dyes containing sulphonic acid groups and their metal complex compounds, which in the metal-free state are of the formula

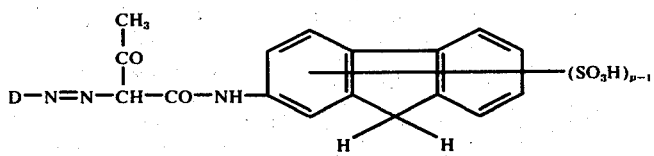

where D represents a radical of the aromatic-carbocyclic or aromatic-heterocyclic series which may be substituted, the dyes of which formula contain 1 to 5 sulphonic acid groups.

Dyes of good quality have in the metal-free state the formula

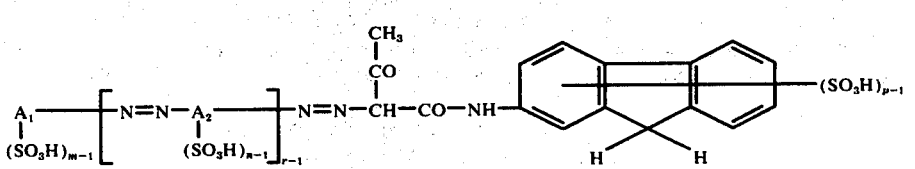

where
  $A_1$ stands for a radical of the aromatic-carbocyclic or aromatic-heterocyclic series which may be substituted or an organic radical bound through an acylacetyl group which may be substituted,
  $A_2$ for a radical of the aromatic-carbocyclic and/or aromaticheterocyclic series which may be substituted,
  $m$ for 1, 2, 3 or 4,
  $n$ for 1, 2 or 3,
  $p$ for 1, 2 or 3,
and
  $r$ for 1 or 2.,
where the sum of $m+n+p$ is 4 to 9.

The new metallizable dyes of formula (II) can be produced by coupling the diazo compound of an amine of the formula

$$D - NH_2 \qquad (IV),$$

with a coupling component of the formula

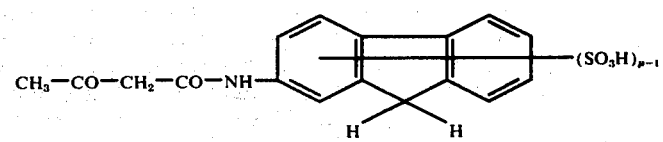

The azo compounds thus obtained can, if desired, be treated with a metal donating compound in substance or in the fibre. The metal-containing azo dyes thus formed may be 1:1 or 1:2 metal complex dyes.

The dyes of formula (III) can be obtained by coupling 1 mole of the diazo compound of an amine of the formula

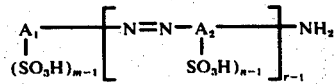

with a coupling component of the formula (V). Monoazo or disazo dyes can be produced by this process. It is preferable for the monoazo dyes of formulae (I), (II) and (III) to contain 1 to 3 and the disazo dyes of these formulae 2 to 4 sulphonic acid groups. All the —SO₃H groups or a proportion of these groups can, however, be replaced by carboxylic acid groups; the dyes may thus bear both —SO₃H and carboxylic acid groups. If the water-soluble azo dyes of formulae (I), (II) and (III) contain metallizable groupings, such as dihydroxyazo, hydroxycarboxyazo or hydroxyaminoazo groupings, they can be treated either in substance or on the fibre with agents donating metal, preferably copper, and so converted into the corresponding metal complex compounds.

Suitable radicals $A_1$ and $A_2$ are optionally substituted aromatic-heterocyclic or aromatic carbocyclic radicals, $A_2$ being preferably an aromatic-carbocyclic radical. As examples may be named benzene, naphthalene, diphenyl, stilbene and fluorous radicals, which besides the aforementioned sulphonic acid and carboxylic acid groups may bear further substituents such as lower alkyl or alkoxy groups, hydroxyl, amino, nitro and cyano groups and halogen atoms, and radicals of the aromatic-heterocyclic series, e.g. benzothiazole and pyrazole radicals. Thiazole, thiadiazole, benzothiazole and pyridine radicals may be named to exemplify heterocyclic radicals. The 2-fluorenyl radical may bear a sulphonic acid group, e.g. in the 1-, 3- or 7-position, or two sulphonic acid groups, one of which is in the 7-position. The lower alkyl and alkoxy radicals contain 1 to 4 or preferably 1 to 3 carbon atoms. In every instance halogen stands for chlorine, bromine or fluorine.

In relation to the nearest comparable dyes, which may likewise be metallized but bear a benzene or naphthalene radical in place of the 2-fluorenyl group, the new dyes of formula (I), (II) and (III) and their metal complex compounds have greater substantivity for cellulosic fibres and better wet fastness. The copper complex compounds in particular show excellent substantivity. The dyestuffs have good fastness to washing, perspiration, sea water, acid, alkali, sulphite, rubbing and formaldehyde.

The amines of formula (VI) may be freely selected from the diazotizable amines, for instance those of the aromatic-heterocyclic or preferably the aromatic-carbocyclic series. The amines of the formula

are exemplified by the following: 4-amino-4'-acetylamino-1,1'-diphenyl or its -3-sulphonic acid; 4-amino-1,1'-diphenyl-4'-sulphonic acid, 4-amino-4'-nitro- or -4'-acetylamino- or -4'-benzoylaminostilbene-2,2'-disulphonic acid, 4-amino-1,1'-diphenyl-3,4'-disulphonic acid, 2-aminofluorene-1, -3- or -7-sulphonic acid, the 2-aminofluorenedisulphonic acids, 2-(4'-aminophenyl)-6-methylbenzothiazole-7-sulphonic acid or -3',7-disulphonic acid.

Amines of formula (VI) in which r is 2 can be produced by coupling 1 mole of the diazo compound of an amine of formula (VII) with 1 mole of a coupling component of the formula

where X represents an the $NH_2$ group, a reducible nitro group or a saponifiable acylamino group, with subsequent reduction of the nitro group, if present, to the amino group, or hydrolysis of the acylamino group, if present, to the amino group.

Azo compounds in which X stands for a reducible nitro group or a saponifiable acylamino group, e.g. acetylamino group, or ethoxycarbonylamino groups, can be converted into compounds of formula (VI) in which r is 2 by treatment with a sodium sulphide or sodium hydrogen sulphide solution with heating, or by hydrolysis at 70°–100° C in acid medium, e.g. 1–10% hydrochloric or sulphuric acid, or in alkaline medium, e.g. 2–10% alkali metal hydroxide solution.

Suitable compounds of the formula (VIII) include amines, nitro derivatives and acylamines of the carbocyclic and heterocyclic series which are capable of coupling; examples are aminonaphthalenes, preferably α-aminonaphthalenes which couple in paraposition to the amino group, hydroxyaminonaphthalenes and hydroxyacylaminonaphthalenes such as 1-aminonaphthalene and its 6- and 7-sulphonic acids, 1-amino- and 1-acetylamino-8-hydroxynaphthalene-3,6- and 4,6-disulphonic acid, 2- and 3-amino- or -acetyl amino-8-hydroxynaphthalene-6-sulphonic acid and 1-(4'-amino- or -nitro)-phenyl-3-methyl-5-pyrazolone.

Diazo compounds of the amines of formula (VI) in which r is 2 can be formed, for example, by coupling 1 mole of the tetrazo compound of a diamine of the formula

with 1 mole of a coupling component of the formula

Dyes of formula (III) in which r is 2 can also be produced by coupling 1 mole of the tetrazo compound of a diamine of formula (IX) with 1 mole of a coupling component of formula (V) and then coupling with 1 mole of a coupling component of formula (X).

Any of the tetrazotizable diamines of the aromatic-carbocyclic and/or aromatic-heterocyclic series can be employed as compounds of formula (IX), for example 4,4'-diamino-1,1'-diphenyl, its 3-sulphonic acid and 3,3'-disulphonic acid, 4,4'-diamino-3,3'-dimethoxy- or -dicarboxy-1,1'-diphenyl, 4,4'-diaminostilbene-2,2'-disulphonic acid, 1-amino-4-(4'-aminophenyl-ureylene)-benzene(4,4'-diamino-N,N'-diphenyl urea), 1-amino-4-(4'-aminophenyl-ureylene)-2,3'-dicarboxybenzene(4,4'-diamino-3,3'-dicarboxy-N,N'-diphenyl urea).

The coupling components of formula (X) may be freely chosen from the compounds capable of coupling, e.g. those of the hydroxybenzene, hydroxynaphthalene, aminonaphthalene, pyrazolone or acylacetylamino series.

Good dyeing properties are shown by compounds of formula (III) in which r is 2 and $A_2$ stands for an aromatic-carbocyclic radical and $A_1$ for an optionally sulphonated 2-acetoacetylaminofluorene radical. These compounds can be produced by coupling 1 mole of the tetrazo compound of a diamine of the formula

where $A_3$ represents an aromatic-carbocyclic radical, with 2 moles of a Representative of the heterocyclic dyes of this application are the compounds of the formula coupling component of formula (V). Other good dyes are of the formula

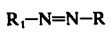 (XIV), where R represents a radical of the formula

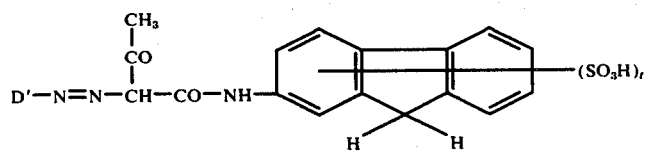

and mixtures thereof,
wherein
D' is

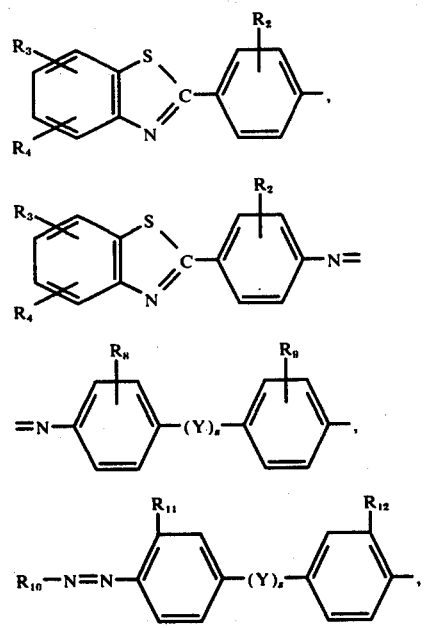

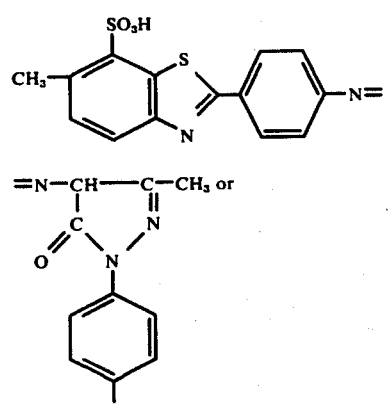

-continued

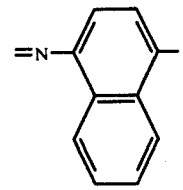

(XII),

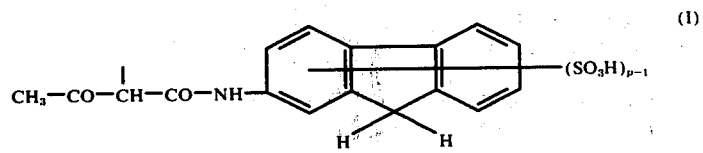

wherein
R$_2$ is hydrogen or sulfo,
R$_3$ is hydrogen, lower alkyl or sulfo,
R$_4$ is hydrogen, lower alkyl or sulfo,
R$_8$ is hydrogen, lower alkyl, lower alkoxy, carboxy or sulfo,
R$_9$ is hydrogen, lower alkyl, lower alkoxy, carboxy or sulfo, with the proviso that when R$_8$ and R$_9$ are sulfo or carboxy they are in the 2,2'- or 3,3'-positions,
R$_{10}$ is 1-phenyl-3-methylpyrazol-5-one-4-yl or 1-(3'-sulfophenyl)-3-methylpyrazol-5-one-4-yl,
R$_{11}$ is hydroxy, carboxy or lower alkoxy,
R$_{12}$ is hydroxy, carboxy or lower alkoxy,
Y is —CH=CH—, —NH—CO—, —CO—NH— or —NH—CO—NH—,
s is 0 or 1, and
t is 0, 1 or 2, with the proviso that the molecule contains 1 to 5 sulfo groups.

and R$_1$ a radical of the formula

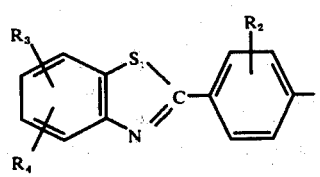 (XV)

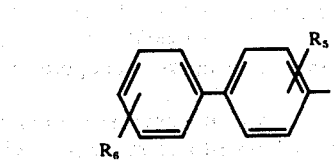 (XVI), in which latter formulae $R_2$ stands for hydrogen or —$SO_3H$, $R_3$ and $R_4$ each stands for hydrogen, lower alkyl such as methyl or ethyl, or for —$SO_3H$, and $R_5$ and $R_6$ each stands for hydrogen or —$SO_3H$.

Equally good dyes correspond to the formula

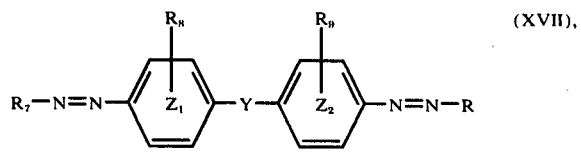
(XVII), where R stands for a radical of formula (I), $R_7$ for a radical of formula (I) or of formula (XV), Y for the direct linkage, —CH=CH—, —NH—CO—, —CO—NH— or —NH—CO—NH—, and $R_8$ and $R_9$ each stands for hydrogen, lower alkyl or alkoxy, —COOH or —$SO_3H$, and where the —$SO_3H$ and/or —COOH group or groups in the rings $Z_1$ and $Z_2$ are in the 2,2'- or 3,3'-position.

Dyes of comparably good quality have in the metal-free state the formula

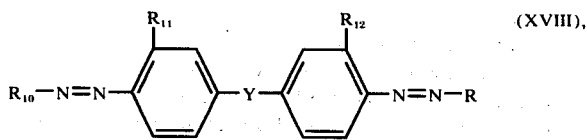
(XVIII), where R stands for a radical of formula (I), $R_{10}$ for a radical of formula (I) or a radical or the pyrazolone series of the series of acetoacetylamino derivatives, and $R_{11}$ and $R_{12}$ for the carboxy or hydroxy group or an alkoxy group. Representative pyrazolone radicals are 1-phenyl-3-methylpyrazol-5-one-4-yl and 1-(3'-sulfophenyl)-3-methylpyrazol-5-one-4-yl.

The copper complex dyes of formula (XVIII) are of notably high quality.

The coupling components of formula (V) can be prepared, for example, by reaction of 2-aminofluorenes or their monosulphonic or disulphonic acids with diketene.

The 2-aminofluorene-11 and -3-sulphonic acids are prepared by dry heat treatment of the acid sulphate of 2-aminofluorenes at temperatures above 180° C, e.g. 200°–300° C. The 2-aminofluore-disulphonic acids can be produced by sulphonation or 2-aminofluorene-1- or -3-sulphonic acid, of 2-aminofluorenes or of 2-aminofluorene-7-sulphonic acid with concentrated sulphuric acid, oleum or chlorosulphonic acid at temperature of 0° C to 200° C.

The diazo or tetrazo compounds and the coupling components used for the production of dyes of the formula (II) or (III) and their metal complex compounds are selected so that the dyes as formed contain the number of water solubilizing groups necessary to impart solubility in water. The water solubilizing groups may occupy any desired positions in the dye molecule.

Diazotization of the amines of formulae (IV), (VII) and (VIII) and tetrazotization of the diamines of formulae (IX) and (XI) can be accomplished by the direct or indirect method in acid medium at temperatures of 1°–10° C or preferably at 0°–20° C.

The coupling reaction with the coupling component of formula (V) can be carried out in weakly acid to weakly alkaline medium, e.g., in the pH region of 4 to 10 or preferably 4 to 6, and at temperatures of −10° C to 100° C or preferably at 0°–40° C, if necessary in the presence of a coupling accelerant such as pyridine, dimethylformamide or urea. On completion of coupling, the dyes are isolated from the solution or suspension by standard methods, for instance acidification and/or precipitation and/or the addition of a suitable water soluble organic solvent such as acetone, acetic acid or an alcohol.

The dyes of formulae (I), (II) and (III) which contain metallizable groups can be treated in substance with agents donating metal, preferably copper, or they can be applied to the fibre and treated there with such agents, again preferably copper donors.

The new dyes and their metal complex compounds are suitable for dyeing and printing textile fibres and textiles of natural and regenerated cellulose, and in particular for dyeing sized and unsized grades of paper which are free from or have a low content of mechanical wood pulp.

On the aforenamed substrates the dyes have good build-up and good levelling properties. On cellulosic fibres they show generally good substantivity and give dyeings with very good wet fastness properties. On paper they are outstandingly fast to water and alcohol and well resistant to acids and alkalis. Their aftercoppered dyeings on cellulosic fibres have good light, wet, rubbing and dry cleaning fastness.

In the following Examples the parts and percentages are by weight and the temperatures are given in degrees centrigrade.

EXAMPLE 1

160 Parts of 2-(4'-aminophenyl)-6-methylbenzothiazole-7-sulphonic acid are suspended in 500 parts of water and dissolved with sodium hydroxide solution. To this alkaline solution is added a solution of 34.5 parts of sodium nitrite in 100 parts of water. The amine settles out in finely divided form and the suspension thus formed is charged at 0°–10° into a mixture of 144 parts of 30% hydrochloric acid and ice. The suspension is stirred further for 2 hours at 0°–10°, after which the excess sodium nitrite is decomposed with aminosulphonic acid.

A solution of 174 parts of 2-acetoacetylaminofluorene-7-sulphonic acid in 1000 parts of water at 50°–60° is prepared and neutralised with sodium hydroxide solution. After it has cooled to 10° the diazo suspension is added, with dropwise addition of 10% sodium hydroxide solution to keep the pH between 7.5 and 8.0. Stirring is continued for a few hours and the temperature allowed to increase to room temperature. Subsequently the dye is precipitated by the addition of 115 parts of 30% hydrochloric acid and 140 parts of sodium chloride.

The dye thus produced dissolves readily in water and gives dyeings of yellow shade on cotton, which have good fastness to light, rubbing, formaldehyde, wet treatments such as washing, sea water, perspiration, alkali, acid and sulphite.

From aqueous solution the dye produces yellow dyeings on paper (sulphite pulp of 40° Schopper-Riegler freeness and tissue paper stock of 18° Schopper-Riegler freeness), which are extremely fast to alcohol and water and show good alkali and acid fastness.

The coupling component used for the dye of this Example can be produced as follows. 283 parts (1 mole) of sodium 2-aminofluorene-7-sulphonate are stirred into 5000 parts of water and dissolved at 90°. On cooling the sodium salt partially settles out. At 65° 100 parts of diketene are added, on which a clear solution is formed. It is allowed to cool to 30°, on which 920 parts of 30% hydrochloric acid are charged into the solution causing precipitation of the acetoacetylamino compound. After continued cooling to 5°–10° the precipitate is filtered off with suction and dried. The yield of the crude product is 328 parts.

EXAMPLE 2

40 Parts of 2-(4'-aminophenyl)-6-methylbenzothiazole-3',7-disulphonic acid are diazotized by the normal method. The excess nitrite is destroyed and the diazo solution added gradually in 15 minutes to a solution of 143 parts of 1-aminonaphthalene, 100 parts of water and 210 parts of glacial acetic acid cooled to 50°. A red monoazo dye is formed which gradually settles out. It is filtered off with suction, stirred into 500 parts of water at 10° and diazotized by the normal indirect method. When diazotization is complete the excess nitrite is decomposed with aminosulphonic acid.

A coupling solution is prepared with 34 parts of 2-acetoacetyl-aminofluorene-7-sulphonic acid, 30 parts of urea and 300 parts of water. 5.2 Parts of glacial acetic acid and 58 parts of sodium acetate are added, on which the coupling component settles out in a fine form. The diazo compound of the aminomonoazo dye is dropped in at an even rate of addition. The coupling reaction sets in slowly, while the pH is maintained at 4.8 to 5.5. After a few hours the yellow-brown disazo dye is completely precipitated by the addition of sodium chloride, filtered off with suction and washed with 10% sodium chloride solution.

EXAMPLE 3

32 Parts of 2-(4'-aminophenyl)-6-methylbenzothiazole-7-sulphonic acid are dissolved in 250 parts of water at 80° and the solution made alkaline with sodium carbonate. After the brown solution has been filtered free from minor impurities 6.9 parts of sodium nitrite are added and it is cooled to 20°. It is then run into a mixture of 28.8 parts of 30% hydrochloric acid and 50 parts of ice. After one hour diazotization is complete and the excess nitrite is destroyed with aminosulphonic acid.

62.5 Parts of a monoazo dye, which is formed by weakly acid coupling of diazotized 1-(4'-aminophenyl)-3-methyl-5-pyrazolone with a mixture of 2-acetoacetylaminofluorene-1,7- and 3,7-disulphonic acids in a 3:2 ratio, are dissolved in 500 parts of water at 20° with the addition of 50 parts of urea. The diazo suspension is allowed to flow into this coupling solution, with the simultaneous addition of sodium carbonate to keep the pH at 7.0 to 7.5. A yellow disazo dye is formed.

EXAMPLE 4

160 Parts of 2-(4'-aminophenyl)-6-methylbenzothiazole-7-sulphonic acid are suspended in 500 parts of water and dissolved weakly alkaline with sodiumhydroxide solution. To this solution is added a solution of 34.5 parts of sodium nitrite in 100 parts of water. The amine settles out in finely divided form to give a suspension, which is run at 0°–10° into a mixture of 144 parts of 30% hydrochloric acid and ice. Stirring is continued for 2 hours at 0°–10°. The excess sodium nitrite is then decomposed with aminosulphonic acid. 174 Parts of 2-acetoacetylaminofluorene-7-sulphonic acid are stirred into 1500 parts of water and dissolved with the addition of 100 parts of urea. 30 Parts of glacial acetic acid and 350 parts of sodium acetate are added, causing the coupling component to settle out in finely divided form. The diazo compound is added at a uniform rate in the space of 20 minutes. Stirring is continued for a few hours, after which the dye is isolated. The dye thus obtained dissolves readily in water and gives dyeings of yellow shade on cotton which have good light fastness, good wet fastness properties (washing, sea water, perspiration, acid, alkali, sulphite) and good fastness to rubbing and formaldehyde.

The dye also dyes paper from aqueous soltuion (sulphite pulp of 40° Schopper-Riegler freeness and tissue paper stock of 18° Schopper-Riegler freeness); the yellow paper dyeings are very fast to alcohol and water and have good alkali and acid fastness.

EXAMPLE 5

43 Parts of 4,4'-diamino-1,1'-diphenyl-3,3'-disulphonic acid are stirred into 400 parts of water, the temperature is increased to 90° and sodium hydroxide solution added to give solution of pH 8.5–9.0. The solution is filtered, 17.5 parts of sodium nitrite are added and it is then cooled to 30°. The suspension is added with thorough stirring to a mixture of 75 parts of 30% hydrochloric acid and 200 parts of ice in the course of 15 minutes. After 2 hours diazotization is complete and the excess nitrite is decomposed with aminosulphonic acid.

88 Parts of 2-acetoacetamidofluorene-7-sulphonic acid and 50 parts of urea are dissolved in 750 parts of water, with the subsequent addition of 15 parts of glacial acetic acid and 175 parts of sodium acetate. The diazo suspension is allowed to flow into the solution. A yellow diazo dye is formed which is filtered off and washed with 10% sodium chloride solution.

The dye dissolves well in water and gives dyeings of yellow shade on cotton which have good light and wet fastness. From aqueous solution the dye builds up well on sized and unsized papers to give yellow dyeings of very good alcohol, water, alkali and acid fastness.

Further examples of dyes which can be produced in accordance with the procedures detailed in the foregoing are set out in the following table. The second column of the table names the monoamines and diamines, the diazo and tetrazo compounds of which are coupled with the coupling components listed in the third column, in any desired order of reaction. The fourth column gives the shade of the uncoppered or aftercoppered dyeing on cotton.

Table

| Exple No | Diazo Component or tetrazo component | Coupling component | Shade of dyeing on cotton |
|---|---|---|---|
| 6 | 2-Aminofluorene-7-sulphonic acid | 2-Acetoacetylaminofluorene-7-sulfonic acid | yellow |
| 7 | 4,4'-Diamino-1,1'-diphenyl-3,3'-disulphonic acid | 2-Acetoacetylaminofluorene-7-sulphonic acid | yellow |
| 8 | 4,4'-Diamino-1,1'-diphenyl-3,3'-dicarboxylic acid | 1)3-Methyl-1-phenyl-5-pyrazolone 2)2-Acetoacetylaminofluorene-7-sulphonic acid | yellow |
| 9 | 1-Amino-4-(4'-aminophenyl-ureylene 2,3'-dicarboxybenzene | 1)3-Methyl-1-phenyl-5-pyrazolone-3'-sulphonic acid 2)2-Acetoacetylamino- | yellow-brown coppered |

Table-continued

| Exple No | Diazo Component or tetrazo component | Coupling component | Shade of dyeing on cotton |
|---|---|---|---|
| 10 | 4,4'-Diaminostilbene-2,2'-Disulphonic acid | fluorene 2-Acetoacetylamino-fluoren-7-sulphonic acid | yellow |
| 11 | 2-Aminofluorene-1-sulfonic acid | '' | yellow |
| 12 | 2-Aminofluorene-3-sulfonic acid | '' | yellow |
| 13 | 2-(4'-aminophenyl)-6-methylbenzothiazole-3',7-disulfonic acid | '' | |

APPLICATION EXAMPLE A

100 Parts of bleached sulphite pulp are beaten with water in a hollander beater. 0.5 Parts of the dye of Example 1 are added and after 15 minutes the sizing agent, which is followed by fixation. Paper manufactured from this stock is dyed in a yellow shade of medium depth with good fastness properties. The backwaters are colourless.

APPLICATION EXAMPLE B

A dyebath is prepared with 2 parts of anhydrous sodium carbonate and 0.5 parts of the dye of Example 1 in 3000 parts of softened water at 30°. 100 parts of a wet-out cotton fabric are entered and the bath is raised to 100° in 30 minutes, with two additions of 10 parts of sodium sulphate at 50 ° and 70°.

After dyeing for 15 minutes at 100° a further 10 parts of sodium sulphate are added and the bath is allowed to cool. The cotton is removed at 50°, rinsed well with cold water and dried at 60°. It is dyed in a yellow shade. The dyeing has good wet fastness properties.

Formulae of representative dyes of the foregoing Examples are as follows:

EXAMPLE 1

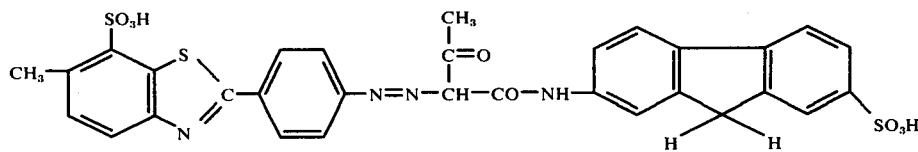

EXAMPLE 3

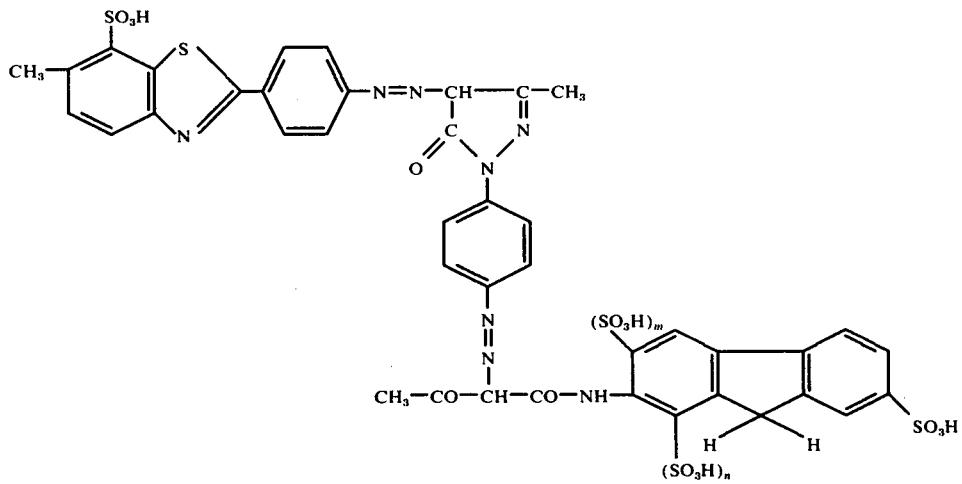

Wherein
$m$ is 0 or 1, and
$n$ is 0 or 1, with the proviso that $m + n$ is 1, and the ratio of compound wherein $n$ is 1 to compound wherein $m$ is 1 is about 3:2.

EXAMPLE 7

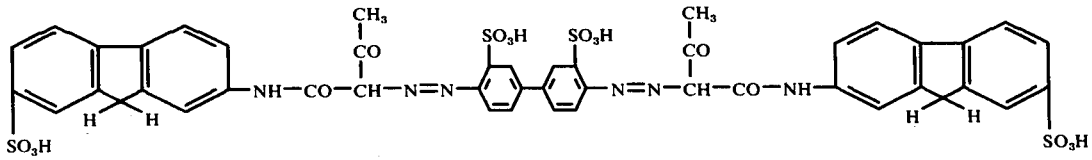

EXAMPLE 8
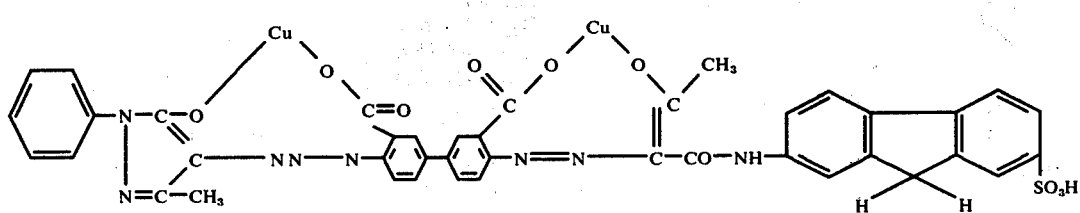
EXAMPLE 11
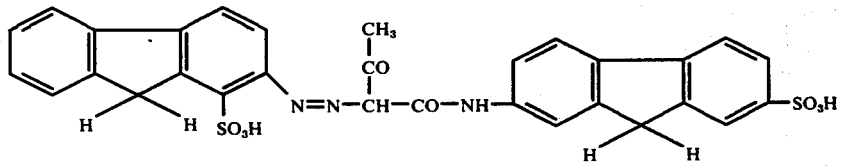
EXAMPLE 12
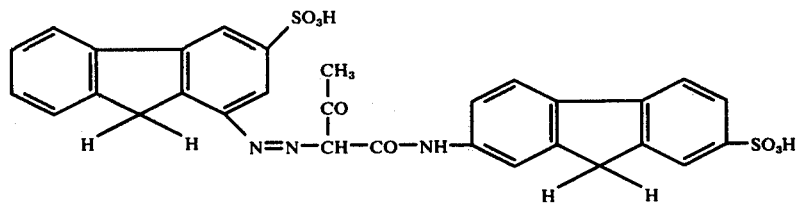
EXAMPLE 13
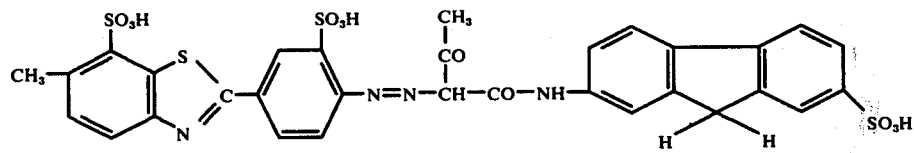
Having thus disclosure what we claim is:
1. A compound of the formula
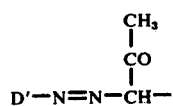
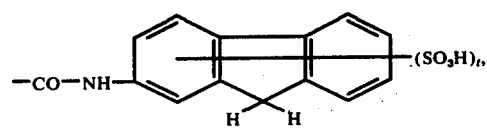
or a mixture thereof,
wherein
D' is
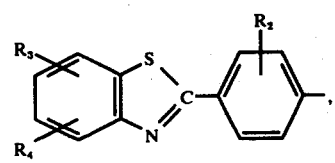
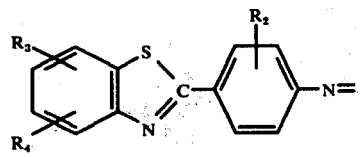
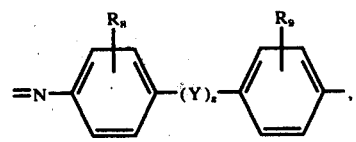
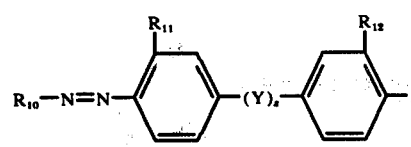
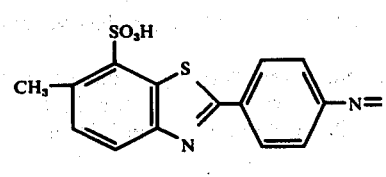

-continued

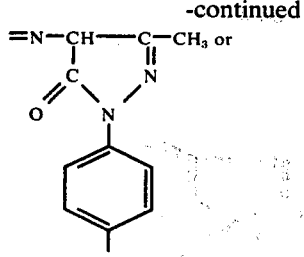

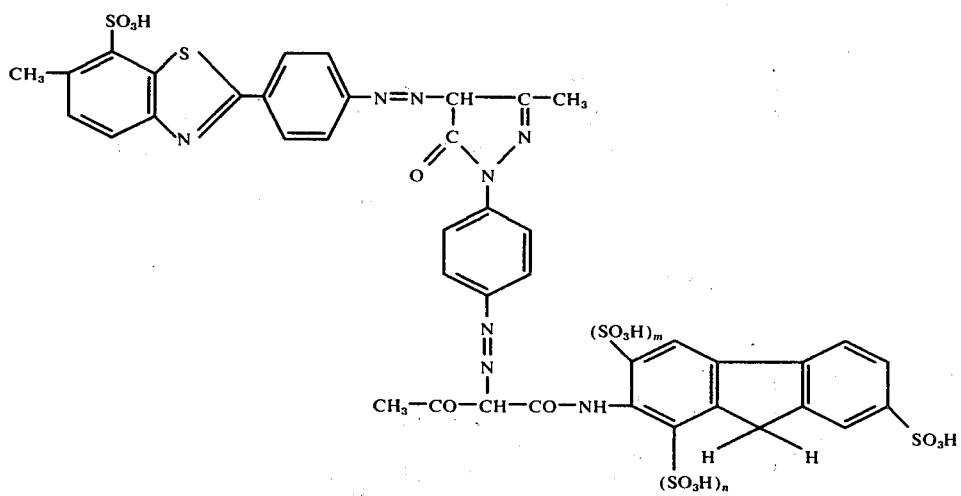

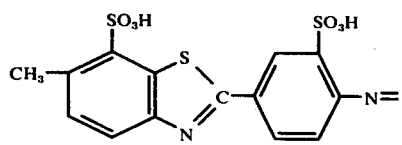

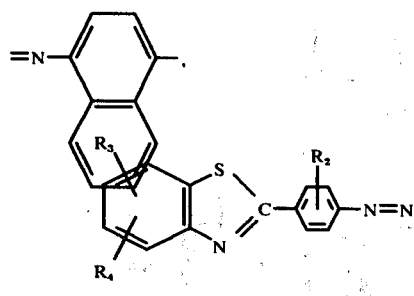

wherein
$R_2$ is hydrogen or sulfo,
$R_3$ is hydrogen, lower alkyl or sulfo,
$R_4$ is hydrogen, lower alkyl or sulfo,
$R_8$ is hydrogen, lower alkyl, lower alkoxy, carboxy or sulfo,
$R_9$ is hydrogen, lower alkyl, lower alkoxy, carboxy or sulfo, with the proviso that when $R_8$ and $R_9$ are sulfo or carboxy they are in the 2,2'- or 3,3'-positions, $R_{10}$ is 1-phenyl-3-methylpyrazol-5-one-4-yl or 1-(3'-sulfophenyl)-3-methylpyrazol-5-one-4-yl,
$R_{11}$ is hydroxy, carboxy or lower alkoxy,
$R_{12}$ is hydroxy, carboxy or lower alkoxy,
Y is —CH=CH—, —NH—CO—, —CO—NH— or —NH—CO—NH—,
$s$ is 0 or 1, and
$t$ is 0, 1 or 2, with the proviso that the molecule contains 1 to 5 sulfo groups.

2. A compound according to claim 1.

3. A mixture of compounds according to claim 1, said mixture being a mixture of compounds of the formula

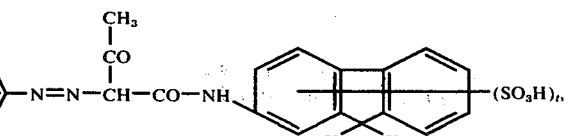

wherein
$m$ is 0 or 1, and
$n$ is 0 or 1, with the proviso that $m + n$ is 1, and the ratio of compound wherein $n$ is 1 to compound wherein $m$ is 1 is about 3:2.

4. A compound according to claim 2 having the formula wherein
$R_2$ is hydrogen or sulfo,
$R_3$ is hydrogen, lower alkyl or sulfo,
$R_4$ is hydrogen, lower alkyl or sulfo,
$R_8$ is hydrogen, lower alkyl, lower alkoxy, carboxy or sulfo,
$R_9$ is hydrogen, lower alkyl, lower alkoxy, carboxy or sulfo, with the proviso that when $R_8$ and $R_9$ are sulfo or carboxy they are in the 2,2'- or 3,3'- positions,
Y is —CH=CH—, —NH—CO—, —CO—NH— or —NH—CO—NH—,
$s$ is 0 or 1, and
$t$ is 0, 1 or 2, with the proviso that the molecule contains at least one sulfo group.

5. A compound according to claim 2 having the formula

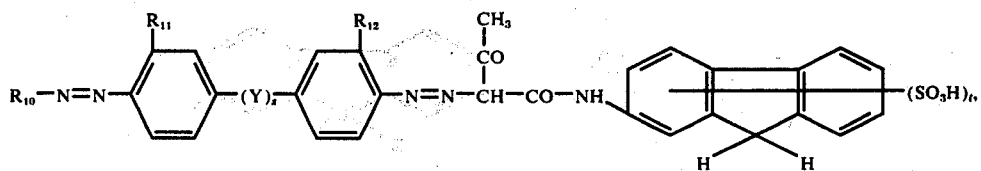

wherein
R$_{10}$ is 4-(1-phenyl-3-methylpyrazolonyl-5) or 4-(1-(3'-sulfophenyl)-3-methylpyrazolonyl-5),
R$_{11}$ is hydroxy, carboxy or lower alkoxy, R$_{12}$ is hydroxy, carboxy or lower alkoxy,
Y is —CH=CH—, —NH—CO—, —CO—NH— or —NH—CO—NH—,
s is 0 or 1, and
t is 0, 1 or 2, with the proviso that the molecule contains at least one sulfo group.

t is 0, 1 or 2, with the proviso that the molecule contains at least one sulfo group.

7. A compound according to claim 6 wherein
t is 1 or 2, with the proviso that when t is 1 the —SO$_3$H group is in the 1-, 3- or 7-position and when t is 2 one —SO$_3$H group is in the 1- or 3-position and the other is in the 7-position.

8. A compound according to claim 7 having the formula

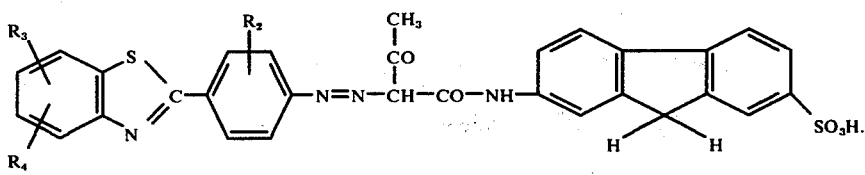

6. A compound according to claim 2 having the formula

9. The compound according to claim 8 having the formula

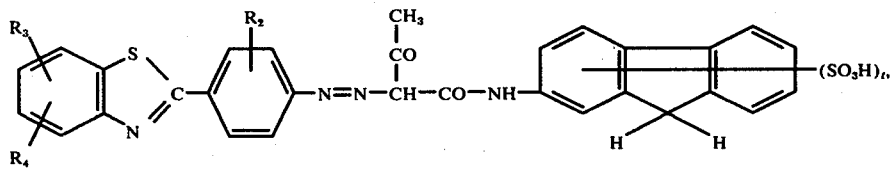

wherein
R$_2$ is hydrogen or sulfo,

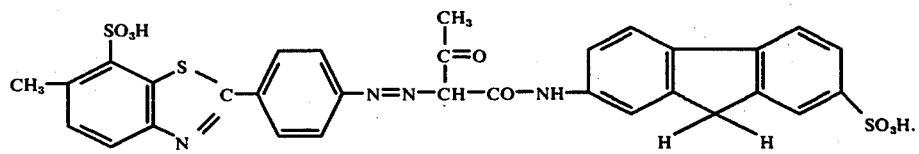

10. The compound according to claim 8 having the formula

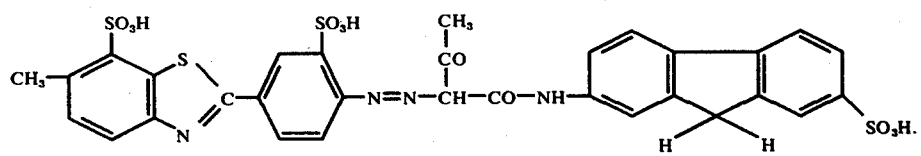

R$_3$ is hydrogen, lower alkyl or sulfo,
R$_4$ is hydrogen, lower alkyl or sulfo, and 11. The compound according to claim 5 having the formula

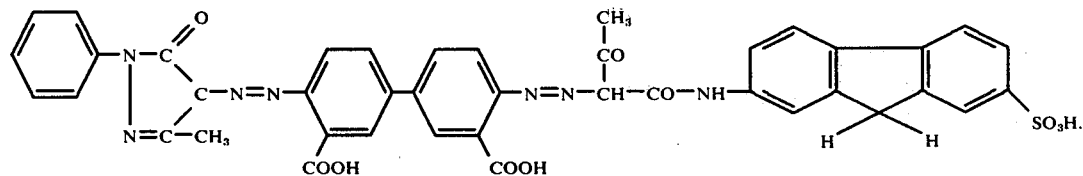
12. The compound according to claim 5 having the formula
13. The compound according to claim 2 having the formula
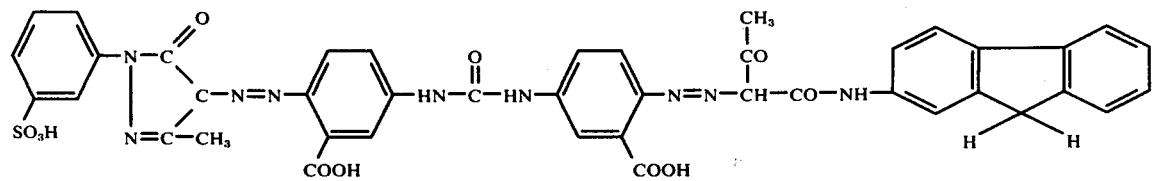
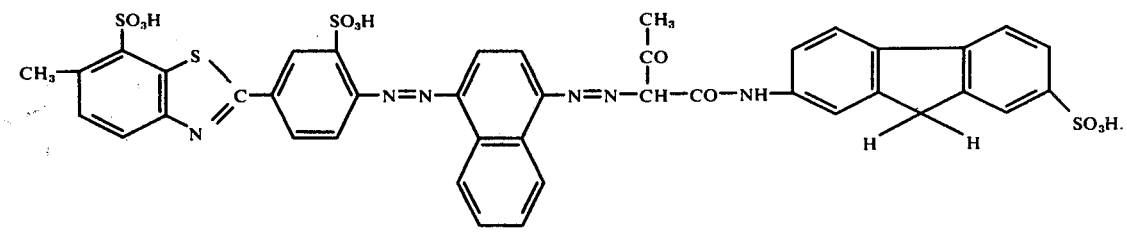
* * * * *